United States Patent
Fernandez-Pol (12)

(10) Patent No.: US 6,589,753 B1
(45) Date of Patent: Jul. 8, 2003

(54) DETERMINING CYTOPLASMIC MSP-1 CONCENTRATION TO AID IN DIAGNOSIS AND PROGNOSIS OF MALIGNANT TUMORS

(76) Inventor: Jose A. Fernandez-Pol, 437 Hunters Hill Dr., Chesterfield, MO (US) 63017

( * ) Notice: Subject to any disclaimer, the term of this patent is extended or adjusted under 35 U.S.C. 154(b) by 0 days.

(21) Appl. No.: 09/124,571

(22) Filed: Jul. 29, 1998

Related U.S. Application Data

(63) Continuation-in-part of application No. 08/580,825, filed on Dec. 29, 1995, now abandoned.

(51) Int. Cl.[7] ............... G01N 33/53; G01N 33/567; G01N 33/574; C12Q 1/44; C12Q 1/46
(52) U.S. Cl. ............... 435/7.72; 435/7.1; 435/7.21; 435/7.22; 435/7.23; 435/7.7; 435/7.71; 435/19; 435/21; 435/40.5; 435/40.51; 435/40.52; 436/63; 436/64; 536/23.5
(58) Field of Search ............... 435/7.23, 7.9, 435/7.1, 7.21, 7.22, 7.72, 7.7, 7.71, 7.92, 19, 21, 40.5, 40.51, 40.52; 436/63, 64; 536/23.5

(56) References Cited

U.S. PATENT DOCUMENTS 5,243,041 A * 9/1993 Fernandez-Pol ............ 536/23.5
5,244,787 A * 9/1993 Key et al. ............ 435/7.9

OTHER PUBLICATIONS

Xynos et al., "Expression of Metallopanstimulin in Condylomata Acuminata of the Female Anogenital Region Induced by Papilloma Virus", Anticancer Research, vol. 14, No. 3A, p 773–786, 1994.*

* cited by examiner

*Primary Examiner*—Anthony C. Caputa
*Assistant Examiner*—Anne L. Holleran

(57) ABSTRACT

An improved method of performing immunohistochemical staining on a tissue sample to determine the presence of cytoplasmic tumor marker Metallopanstimulin in cells in the tissue sample. The method consists of generally of collecting the tissue sample; fixing the tissue sample in a manner that preserves the Metallopanstimulin in the cytoplasm of the tissue cells; embedding the sample in paraffin; deparaffinizing the tissue; heating the sample to expose antigenic sites; incubating the slide with a stain blocking agent; incubating the tissue with a primary anti-Peptide A antibody having an affinity for the N-terminal portion of the Metallopanstimulin; incubating the sample with chromogen stain; rinsing the sample; dipping the slide in a counterstain; mounting the slide for reading. Materials for performing the above steps are provided in a convenient, reasonably priced kit.

2 Claims, 2 Drawing Sheets

DETERMINING CYTOPLASMIC MSP-1 CONCENTRATION TO AID IN DIAGNOSIS AND PROGNOSIS OF MALIGNANT TUMORS

CROSS REFERENCE TO RELATED APPLICATIONS

This application is a continuation-in-part of application Ser. No. 08/580,825, filed Dec. 29, 1995, now abandoned.

STATEMENT OF GOVERNMENTAL INTEREST

None

BACKGROUND OF THE INVENTION

This invention relates generally to medical diagnostics and, more specifically, to a method of diagnosing and staging malignant tumors using an improved method of immunohistochemistry to determine the concentration and distribution of a cytoplasmic tumor marker associated with malignant tumors.

The inventor has previously identified, by cDNA cloning, a gene denoted Metallopanstimulin (MPS-1). The novel DNA sequence which encodes the MPS-1 is disclosed in U.S. Pat. No. 5,243,041 (Re. 35,585), issued Sep. 7, 1993, the disclosure of which is hereby incorporated by reference. The recombinant MPS-1 protein and chemical derivatives can be used to generate polyclonal and monoclonal anti-MPS-1 antibodies. The MPS-1 gene is expressed at high levels in numerous human carcinoma cell lines such as prostate, breast, brain, lung, and particularly melanomas. It is also expressed in human hematological malignancies. MPS-1 is a multifunctional S27 ribosomal protein that is involved in cellular proliferation and oncogenesis in numerous human neoplasms. The MPS-1 gene is expressed at high levels in numerous human carcinoma cell lines such as breast, prostate, colon, brain, lung and melanoma. Table IA indicates the presence of MPS-1 mRNA in cultured human malignant cell lines and in peripheral blood of human patients with hematological malignancies. Cytoplasmic MPS-1 is of particular interest because of the proliferation of cytoplasmic mRNA in proliferative diseases, including cancers. Table 1B indicates the presence of MPS-1 mRNA in human hematological malignancies.

TABLE 1A

PRESENCE OF MPS-1 mRNA IN CULTURED HUMAN MALIGNANT CELL LINES

| Cell type | Cell line |
| --- | --- |
| Breast carcinoma | MDA-MB-468, MDA-MB-231, BT-20 |
| Prostrate carcinoma | DU-145, PC-3 |
| Melanoma | SK-MEL-28, RPMI-7951 |
| Colon adenocarcinoma | LoVo |
| Lung carcinoma | A-549 |
| Vulvar carcinoma | A-431 |
| Fibrosarcoma | HT-1080 |
| Neuroblastoma | LAN-5 |
| Squamous cell carcinoma of skin | SCC-15 |

TABLE 1B

PRESENCE OF MPS-1 mRNA IN HUMAN HEMATOLOGICAL MALIGNANCIES

| | MPS-1 mRNA | |
| --- | --- | --- |
| Type of Malignancy | Negative | Positive |
| Presence of Malignant cells in peripheral blood | | |
| Chronic lymphocytic leukemia | 0 | 3 |
| Chronic myelogenous leukemia | 0 | 2 |
| Multiple Myeloma | 0 | 3 |
| Lymphoma | 0 | 3 |

Table 2 illustrates the results of tests conducted to detect MPS-1 mRNA and protein in human tissues.

TABLE 2

DETECTION OF MPS-1 mRNA AND PROTEIN IN HUMAN TISSUES

| Type of Tissue | No. of samples mRNA[1]/Protein[2] | Organ of Origin |
| --- | --- | --- |
| A. CARCINOMAS AND SARCOMAS | | |
| Carcinoma | 52+++/+++ | Vulva, Cervix, Ovary Endometrium, Colon, Lung, Bladder, Liver Metastatic |
| Squamous Cell Carcinoma | 35+++/+++ | Vulva, Cervix Esophagus, Lung, |
| Adenocarcinoma | 25++/++ | Cervix, Ovary, Endometrium, Colon, Prostate |
| Carcinoma In Situ | 9++/++ | Vulva |
| Serous Carcinoma | 5+/+ | Ovary |
| Papillary Serous Carcinoma | 5++/++ | Endometrium |
| Sarcoma | 4++/++ | Ovary, Endometrium, metastasis |
| Melanoma | 2>+++/+++ | Vulva, Metastasis |
| Verrucus Carcinoma | 1++/++ | Vulva |
| Retroperitoneal Liposarcoma | 1+++/+++ | Retroperitoneal |
| Mucinous Carcinoma | 1+/+ | Ovary |
| Leiomiosarcoma | 1++/++ | Ovary |
| Papillary Carcinoma | 1++/++ | Ovary |
| Papillary Adenocarcinoma | 1++/++ | Endometrium |
| Adenosquamous Carcinoma | 1++/++ | Endometrium |
| Clear Cell Carcinoma | 1++/++ | Endometrium |
| Mixed Mesodermal Carcinoma | 1+/+ | Endometrium |
| Mixed Mullerian Tumor | 1+/+ | Endometrium |
| Ductal Carcinoma | 3+++/+++ | Breast |
| Inflammatory Carcinoma | 1>+++/+++ | Breast |
| B. BENIGN LESIONS | | |
| Lichen Sclerosus atrophicus | 1−/− | Vulvar Skin |
| Benign Cysts | 10ND/− | Ovary, Breast |
| Granuloma | 1ND/+ | Lung |
| Leiomyoma | 2ND/− | Uterus |
| Fibroma | 1ND/− | Ovary |
| C. NORMAL TISSUES[3] | 63−/− | Cervix, Ovary, Endometrium, Myometrium, Vagina, Peritoneum, Fallopian Tubes, Breast, Rectal Muscles, Skin, Small Intestine, Lymph Node |

Table 2 should be read as follows:
Signals: (−) negative, (+) weakly positive, (++) positive, and (+++) strongly positive. The stainings recorded refer to that of the cancer cells, since the stroma cells were not significantly stained. Note that although normal tissues are listed as (−), they showed staining (+ to +++) only in areas of normal cell proliferation. ND: Not done. Note that (i) vulvar melanoma, and breast inflammatory carcinoma had the highest levels of MPS-1 mRNA and protein detected; by Northern blot analysis the MPS-1 mRNA levels in these tissues were >80-fold normal levels; and (ii) lichen sclerosus atrophicus, a rare condition characterized by extremely low proliferation rates was negative for MPS-1 mRNA and protein in the usual areas of cell multiplication; these observations are highlighted by bold characters.

The inventor has determined that there is a high correlation between a patient's survival rate and the level of cytoplasmic MPS-1 observed. That is, the patient's survival rate decreases in proportion to increased concentration distribution of cytoplasmic MPS-1 detected. Hence, the method of the present invention is useful as a prognostic indicator of disease progress and survival.

The MPS-1 mRNA was detected using biotynilated single-stranded anti-sense DNA probe. The MPS-1 protein was detected by immunohistochemical staining using anti-peptide A antibodies. As can be observed, there is an excellent correlation between the concentration and distribution of MPS-1 mRNA and protein expression. In contrast, the MPS-1 gene is expressed at low levels in normal cells. The results of experiments indicated that the MPS-1 antigen is a ubiquitous tumor marker which is useful in detection, prognosis and management of various types of neoplastic conditions, particularly when the concentration and distribution of the protein is detected in the cytoplasm, as recently discovered.

Although the detection and management of all forms of cancer is desirable, the detection of malignant melanoma is particularly challenging to the clinician. Often benign lesions are difficult to distinguish from malignant lesions. It is imperative, however, that cancers such as malignant melanoma, breast cancer and prostate be detected early and reliably to improve survival rates.

Recently, immunohistochemical studies were conducted to examine the expression of MPS-1 protein in various types of benign and malignant melanocytic lesions. Protein antigen, detected with anti MPS-1 antibodies was found in both benign and malignant melanocytic lesions. The anti-MPS-1 antibodies directed to the N-terminal portion of the molecule are most useful. In benign lesions, the staining was weak and in a gradient, the most superficial cells with nesting growth patterns were positive, particularly those within the epidermis. The stain intensity decreased as the melanocytes were located deeper in the dermis. Practically speaking, only type A melanocytes stain positive while the B and C types are negative.

Recurrent melanocytic nevi were also studied. MPS-1 was nearly negative in the original untreated nevi. In the recurrent lesions, the regenerating epidermal and dermal melanocytic components were intensely and evenly stained. These findings were very similar to those seen in melanomas. These changes are an example of intense activation of the newly formed melanocyte population and not a sign of malignant transformation.

It is of interest to note that scar tissue generates large amounts of growth factors. Thus, growth factors may be responsible for both activation of melanocytic cells and intense expression of MPS-1 observed in the incomplete biopsy. It will be appreciated that the histological features of these recurrent nevi were indistinguishable from melanomas, a phenomenon that often confounds the diagnostician. The correct diagnosis was made by reviewing the original melanocytic nevus.

In three of the Spitz's nevi studied, two were weakly positive or negative. Interestingly, those lesions occurred in adults. The third lesion was strongly positive and occurred in a two year old child. The most interesting findings were seen in congenital nevi, These lesions have a similar gradient staining as seen in regular nevi but also had discrete MPS-1 positive nodules contrasting with negative ones as seen in melanomas. These findings reveal a heterogeneous (clonal?) cell population and reflect, perhaps, an unstable cell population. This is of interest in view of the fact that congenital nevi are at times precursors of melanoma.

In melanomas, the staining patterns are more complex. While some melanomas stain evenly positive, others have remarkable variable expression of MPS-1. This seems to correlate, to some extent, with intralesional transformation. The variability is so pronounced that some cells stain intensely positive in nests of cells staining moderately positive. The scattered melanocytes migrating to the upper layers of the epidermis usually are intensely positive. Curiously, metastatic melanoma to lymph nodes shows only faint positivity in the limited sampling studied. A single example of melanoma metastatic to the skin was evenly and intensely positive in spite of its seemingly well differentiated, almost nevoid appearance. No gradient staining was present, as it should have been in the case of a benign nevus. Thus, the inventor has determined that the novel test described and claimed herein has widespread application in the diagnosis of melanocytic lesions of the skin (Santa Cruz et. al Differential expression of Metallopanstimulin/S27 ribosomal protein in melanocytic lesions of the skin, J. Cutan Pathol 1997; 24:533–542).

Macrophages in and around the area are intensely positive with a coarse, granular cytoplasmic pattern. Macrophages present in less intensely stained areas had less MPS-1 content than those located in strongly stained areas. This was particularly true in nevi in which macrophages were rare or non-existent. This finding tends to correlate with the near absence of apoptosis in nevi. On the other hand, the presence of MPS-1 in macrophages of melanomas suggests direct phagocytosis of melanoma cell debris following apoptosis, a common phenomenon. Some melanocytes in melanomas show individual cells with similar patterns, supporting the concept of phagocytosis by melanoma cells.

MPS-1 also stains reactive acanthotic epidermis, sebaceous glands and the secretory portion of the sweat glands. Hair follicles also are positive in a gradient, with the more mitotically active cells of the matrix staining the strongest. Basal cell carcinomas show even moderate positivity. As the above discussion points out, MPS-1 is an extremely useful marker for melanocytic lesions at the immunohistological level, providing important clues in the biological nature of melanocytic tumors not obtainable by other methods. Also, as stated above, the MPS-1 is a useful prognosticator of patient survival.

It was suggested in Example 12 of U.S. Pat. No. 5,243,041, col. 35, line 14, that antibodies to MPS-1 bind to melanoma cells. Furthermore, it was suggested therein that antibodies that bind to MPS-1 may have diagnostic uses. It also will be appreciated that Example 12 contemplates using antibodies to the MPS-1 protein prepared by the method of Example 11. While the examples listed work well for their intended purposes, which was to show a gross correlation between MPS-1 and cancer and to demonstrate the potential utility of MPS-1 as a tumor marker, the procedures of Example 12, in addition to being generally highly complex, were experimental and lacked any immediate practical application for the clinician.

More importantly, the procedures disclosed in the '041 patent, as well as in the inventor's paper (Xynos et al; Anticancer Res. 14:773–786 1994) do not have the widespread clinical applicability of the present invention. First, the procedure disclosed in the '041 patent and in Xynos et al detects the presence of MPS-1 protein in nuclear material. As set out above, this test had little practical application and was useful to demonstrate that MPS-1 could be considered a ubiquitous tumor marker. The inventor subsequently determined there is little correlation between nuclear staining intensities and elevated MPS-1 levels associated with cancer. Thus, the original techniques had little diagnostic or predictive value. Because the prior art tests detect the presence of MPS-1 proteins in the nucleus, the number of false positive results are elevated. This is because MPS-1 proteins may be found in the nucleus, even in non-malignant cells, and because the prior art methods resulted in a loss of cytoplasmic MPS-1 from the cell membrane. The prior art methods included the use of a detergent, saponin, caused a "washing out" of cytoplasmic MPS-1 and the concomitant staining of nuclear proteins. The chromogenic reaction described in the patent at col. 33, lines 40–43, included the use of Naphthol phosphate/Fast Red TR, which penetrated into the nuclear proteins and resulted in staining of the nuclear proteins. The staining of the nuclear proteins in the prior art methods make distinguishing between normal cells and early cancers very difficult. The inventor later discovered that in malignancies there is elevated MPS-1 protein in the cytoplasm due to the elevated levels of proteins having a recognizable N-terminal portion produced as a ribosomal protein. Moreover, he determined that there is an increase in ribosomal MPS-1 proteins in the cytoplasm that is related to the stage of the cancer. The methods of the present invention conserve cytoplasmic MPS-1 which eliminates the false positive or non-quantifiable detection of nuclear MPS-1 of the old methods. Determining the level of cytoplasmic, i.e. ribosomal MPS-1, is the key to a detecting and staging cancers and the prediction of disease free survival. Thus, the present invention can be used to determine prognosis based upon the amount, i.e. concentration and distribution, of cytoplasmic MPS-1 protein detected.

Furthermore, the procedures outlined in Example 12 are not easily or cost-effective practiced by a diagnostician, in the hospital or in the medical office, to test a tissue sample. I have devised a low cost, simple to use method and kit for practicing the method that takes advantage of the fact that MPS-1 provides a useful marker, but does so in a way not shown or suggested by the U.S. Pat. No. 5,243,041, or any other reference known to the inventor. In addition, the use of a poorly visualized dye as described in Example 12 of the '041 with melanoma produced only a slightly different brown rendering interpretation of the results extremely difficult.

In summary, the prior art immunohistochemistry procedures lack specificity. The sensitivity is low and the procedures have relatively poor predictive functions. The prior art tests also have high background staining which results in difficult differentiation. In addition to proving the efficacy of the novel immunhistochemistry techniques of the present invention as applied to melanoma, the inventor has demonstrated that the new method of detecting Metallopanstimulin expression in stages I and II breast cancer correlates with clinical and pathological factors. The prior art immunohistochemistry techniques disclosed by the inventor were not satisfactory for detecting breast cancers. The differential expression of MPS-1 in Stage I and Stage II were difficult to analyze because the perceived differences between stained tissue and background were minimal and, because of the permeability of the cells, nuclear protein staining obfuscated the importance of cytoplasmic MPS-1. Furthermore, there is a clinical relationship between the differential expression of Metallopanstimulin in hepatic regeneration and liver oncogenesis. The expression of the Metallopanstimulin (MPS-1) in the cytoplasm in breast and liver disease was studied in tissue samples by immunohistochemistry of the present invention using specific anti-MPS-1 antibodies. The concentration and distribution of cytoplasmic MPS-1 correlates well with disease free survival this provide a reliable prognostic tool.

SUMMARY OF THE INVENTION

It is among the several objects of the invention to provide a novel method of performing immunohistochemical staining of a tissue sample to detect cancer cells.

It is also among the several objects of the invention to provide a simple method of performing immunohistochemical staining of a tissue sample to detect the expression of Metallopanstimulin (MPS-1) in cancer cells.

It is another object of the invention to provide a such a method that avoids loss of cytoplasmic Metallopanstimulin.

It is another object of the invention to provide a such a method that allows the detection of the Metallopanstimulin in the cytoplasmic region.

Another object of the invention to provide a such a method that allows the quantification of the concentration and distribution of Metallopanstimulin in the cytoplasmic region It is another object of the invention to provide a such a method that allows the detection of the Metallopanstimulin in the cytoplasmic region so as to avoid false positives associated with nuclear staining.

Another object of the invention is to provide a method of determining the concentration and distribution of the Metallopanstimulin in the cytoplasmic region of suspected malignant cells to allow quantification, grading or staging of the disease.

Another object of the invention is to provide such a method that employs antibodies directed to the N-terminal portion of the MPS-1 protein.

Another object of the invention is to provide a method of performing immunohistochemical staining wherein the dye renders the Metallopanstimulin easy to visualize.

It is another object of the invention to provide a simple method of performing immunohistochemical staining of a tissue sample using antibodies prepared by using synthetic peptides with partial MPS-1 sequences.

It is another object of the present invention to provide a method of performing immunohistochemical staining of a tissue sample that can be easily performed by a diagnostician in the hospital or office setting.

Still another object of the present invention is to provide the materials needed to perform the novel immunohistochemical staining technique in a simple to use, reasonably priced kit.

In accordance with the invention, a method of performing immunohistochemical staining on a tissue sample and the materials for doing the same are provided. The method is directed to the detection of MPS-1 proteins in the cytoplasm with antibodies directed to the N-terminal portion of the MPS-1 protein. Staining techniques allows the visualization of antibody-protein complexes. The antibody-protein complexes can be quantified to allow gradation of the malignancy. The method avoids the loss of cytoplasmic proteins and avoids which can cause false positive readings, unquantifiable results, and artifacts.

The method consists of preparing a sample holder, which in the embodiment illustrated is a glass slide, with a reagent bonding material; collecting the tissue sample; fixing the tissue sample; embedding the sample in paraffin; deparaffinizing the tissue; preparing the tissue for staining; incubating the slide with a stain blocking agent; incubating the tissue with a primary anti-Peptide A antibody produced in accordance with the procedures described in U.S. Pat. No. 5,243,041 (Re. 35, 585); incubating the sample with red chromogen stain; rinsing the sample; dipping the slide in a standard bluing solution; mounting the slide for reading. The materials for performing the above steps are provided in a convenient, reasonably priced kit.

DESCRIPTION OF THE PREFERRED EMBODIMENT

Figure 1:
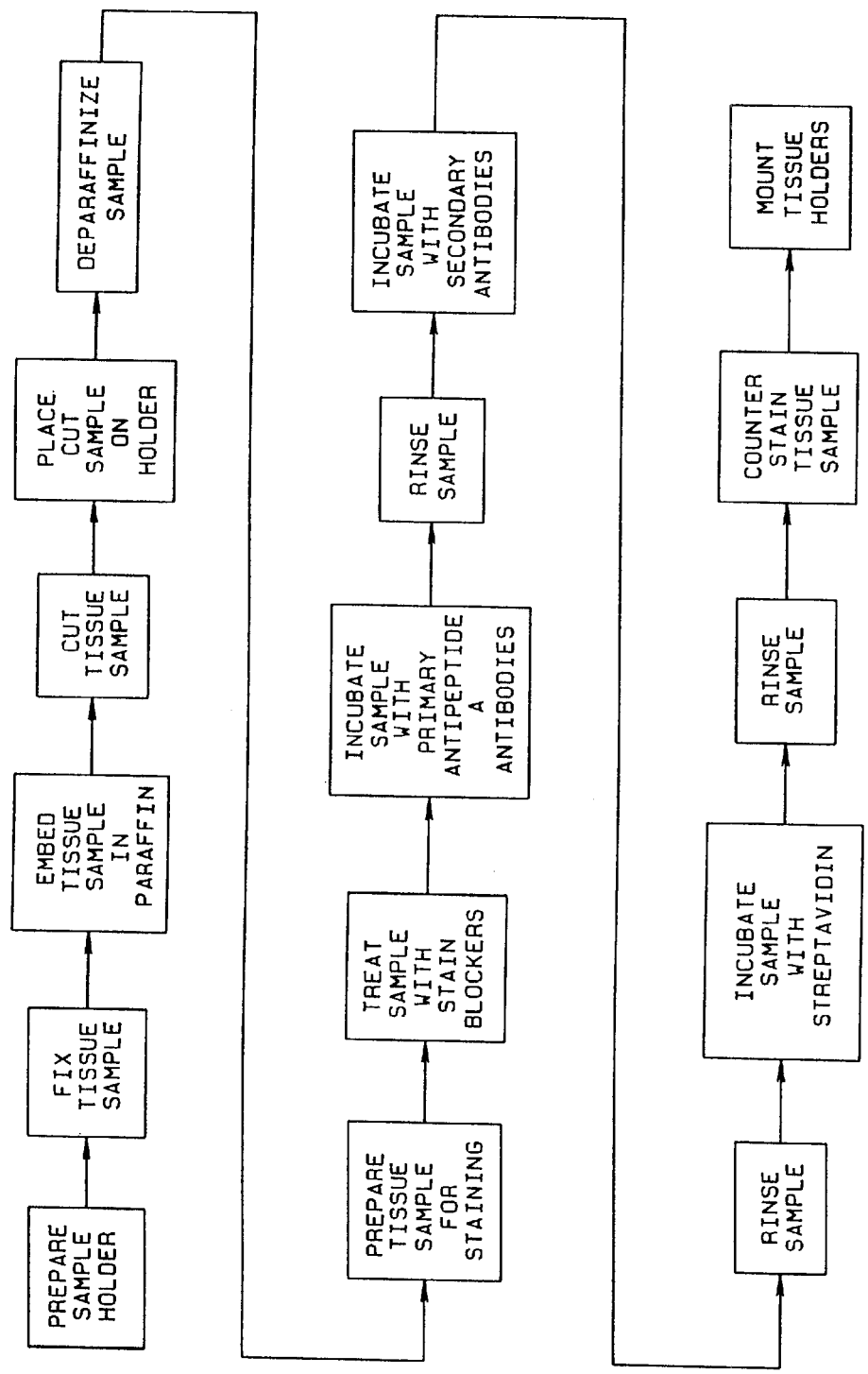
FIG. 1 is a flow chart illustrating the steps of the method of the present invention.

The present invention comprises an immunohistochemistry procedure for the detection of MPS-1 protein in the cytoplasm of cells. The present invention avoids the washing out of cytoplasmic MPS-1 which results the staining only of nuclear proteins giving false positive readings, unquantifiable results and/or artifacts. The invention includes preparation of the tissue sample; exposure of the prepared sample to a first antibody with an affinity for the N-terminal portion of the MPS-1 protein; exposure of the resulting antibody/N-terminal complex to a second antibody with an affinity for the first antibody; staining the resulting antibody/antibody complex with a highly visible red dye; visualization of the stained antibody/antibody complex; and quantification of the stained complex. The resulting quantification of the stained complex allows gradation of the malignancy because the amount of cytoplasmic or ribosomal MPS protein is in proportion to the progress of the underlying cancer.

One preferred embodiment of the present invention can be described generally as follows:

Immunohistochemistry assays to detect the localization of MPS-1 protein are performed on routinely processed formalin-fixed paraffin embedded tissues. The method employs localization of the MPS-1 antigen using anti-MPS-N terminus antibodies through the Biotin-Streptavadin Amplified System (StrAvGen™, Biogenex, San Ramon, Calif.). The second antibody link is biotinylated and streptavidin is conjugated to alkaline phosphatase which generates a chromogenic reaction with appropriate reagents. Each tissue section analyzed for the presence of the MPS-N antigen is analyzed in parallel with a contiguous section from the same tissue in which the primary anti-peptide N antibody is omitted as a control.

Histological sections are mounted on sylane coated slides and deparaffinized with xylene. After clearing the slides in ethanol, they are placed in a citric acid buffer solution (pH 6) and boiled in a microwave over for two periods of 5 minutes each. The heating step exposes the antigenic sites. After blocking the endogenous peroxidases with methanol and 1% hydrogen peroxide, sections are incubated with normal rabbit serum diluted 1:20 for 20 minutes. After decanting the serum, sections are incubated overnight at 4° C. with the primary antibody. The slides then are washed in a phosphate buffered saline and incubated with the appropriate diluted secondary biotinylated ant-rabbit or anti-mouse antibodies for 40 minutes, followed by avidin-biotin complex (ABC, Vector Laboratories, Burlingame, Calif.) diluted 1:150. Sections are developed with diaminobenzidine and hematoxylin counterstain.

Generally speaking the expression of the MPS-1 protein is enhanced in malignancies. Therefore, increased cytoplasmic staining is observed. A semiquantitative estimation of MPS-1 immunoreactivity can be performed. For example, a score can be given to each slide, considering the intensity of the cytoplasmic stain. If there is no staining, a 0 score can be given. A+1 score indicates weak staining, a+2 score indicates moderate staining, and a+3 score indicating strong intensity of staining. As will be appreciated, any scoring scheme used to compare staining intensities may be used as long as it takes into account the relative intensity of cytoplasmic staining and allows differentiation among degrees of intensity of staining, thus providing a way to grade the malignancies. Because of the novel staining aspects of the present invention which results in highly differentiated staining, the scoring or grading can done visually, thus allowing the technique of the present invention to be widely used clinically without sophisticated equipment. However, it will understood that the staining results can be analyzed by appropriate sensitive optical equipment and analyzed by computer.

One preferred method of performing immunohistochemistry staining of tissue using antibody to peptide A sequence of Metallopanstimulin (MPS-1) is best illustrated, by FIG. 1 and by the following example:

EXAMPLE

1. Glass Slide Preparation

Glass slides are treated with APES/acetone reagent, for example as provided as Vectabond, Vector Labs., Burlingame, Calif., according to the manufacturer's protocol.

2. Collection of Tissue Samples

The preferred fixing solution is 10% buffered formalin. However, tissues fixed with the conventional buffered formalin require antigen retrieval by microwaving, as described below.

An alternative fixing solution is zinc-formalin, for example available from Shandon, Pittsburg, Pa. After the tissues are fixed in zinc-formalin, tissues are rinsed in regular 10% buffered formalin. The tissues then are processed by conventional procedures and embedded in paraffin. This method uses saponin and will result in increased nuclear staining. This method is not preferred for predictive or quantifiable results but can be used to detect nuclear proteins.

3. Tissue Cutting

Tissues are cut to approximately 5 micron thickness and floated onto the treated glass slides in an approximately 42° C. water bath. The tissues are allowed to dry at room temperature. Next, the slides are heat-fixed at approximately 56° C. for approximately one hour. The slides then can be stored at approximately 4° C. until used.

4. Deparaffinization

Tissues are deparaffined by 5 minute rinses as follows:
a) two (2) rinses with xylene;
b) two rinses with 100% ethyl alcohol (EtOH);
c) one rinse with 95% ethyl alcohol (EtOH);
d) one rinse with 70% ethyl alcohol (EtOH);
e) one rinse with 50% ethyl alcohol (EtOH); and
f) water rinse.

5. Preparation for Staining

Treatment of the slides after deparaffinization depends on the method of fixation:
a) Formalin fixed tissues: Tissues are microwaved three (3) times for 5 minutes each time in a 10 mM sodium citrate buffer, pH 6.0. The 5 minute time is based upon a 750 watt microwave oven with four 60 ml plastic 5-slide coplin jars with the slides in the jars. Times may vary between microwaves. The samples are microwaved to expose the antigenic sites. A constant volume of citrate buffer always should be used regardless of the number of slides being processed. Add approximately 5 ml of citrate buffer between microwaving times to bring the volume up to 60 ml and keep the tissues covered. After microwaving, cool the slides at room temperature for 20 minutes and then rinse one time in the PBS. The preferred embodiment of the present invention includes this step to avoid the washing out of cytoplasmic proteins.
b) Zinc-formalin fixed tissues: Tissues are placed in 0.05% Saponin for 30 minutes at room temperature. Next, they are rinsed three (3) times with phosphate buffered saline (PBS) plus magnesium and WITHOUT CALCIUM, for example, Dulbecco's Buffered Saline, Gibco Life Technologies, Inc. Grand Island, N.Y. The inventor has determined that the use of phosphate buffered saline without calcium is critical so that calcium dependent enzymes in the sample are not induced at this stage. After the final rinse and before the addition of reagents, excess liquid is removed from the slides. This can be accomplished by tapping the slide on a paper towel and by careful aspiration of the liquid around the tissue. As stated above, this step can result in the washing out of the cytoplasmic proteins due to the use of the detergent, saponin and is included as an alternative embodiment if nuclear staining is desired.

6. Incubation a) The slides are incubated with 100 µl of avidin, for example as provided in Blocking Kit, Vector Labs., Inc. Burlingame Calif. 94010, to eliminate non-specific staining due to endogenous biotin. Next, the slides are rinsed three (3) times in PBS. The slides are incubated for 20 minutes in 100 µl biotin also as provided in Blocking Kit, Vector Labs., Inc., with 10% normal goat serum, for example available from Vector Labs., Inc., added. The slides then are rinsed three (3) times with PBS.

Next, the slides are incubated with 100 µl of a primary anti-peptide A antibody for 60 minutes at room temperature in a humidified container. Primary anti-peptide antibody A is omitted in one slide as a control.

The anti-peptide A antibodies are prepared in accordance with procedures disclosed in U.S. Pat. No. 5,243,041 (Re. 35,585) and are antibodies against peptide (amino acid sequences) shown in FIG. 3 of that patent. The anti-peptide A stock solution of antibody can be prepared by reconstituting lyophilized antibody to yield a final concentration of 800 µg/ml in sterile water containing 0.2% sodium azide to reconstitute the antibody. The standard dilution of the reconstituted stock antibody is 1:100 in 1% bovine serum albumin available, for example from Sigma Chemical, St. Louis, Mo., in PBS buffer. This will yield a final concentration of 8 µg/ml. The anti-peptide A antibodies are prepared from a peptide antisera against the amino terminus of the MPS-1 protein having a sequence PLAKDLLHPSPEEEKR, designated as the N-terminus peptide corresponding to segment amino acid segment amino acid number 2 to amino acid number 17 of SEQ. ID. No. 2, U.S. Pat. No. 5,243,041 (Re. 35, 585). The N-terminus peptide is derived from the N-terminal region of the protein, located between the N-terminus and the zinc finger domain. In the preferred embodiment, the N-terminal peptide is selected so that it does not contain any portion of the zinc finger domain of the MPS-1 protein because the zinc finger domain is a highly conserved structure and antisera against it might cross-react with other zinc finger proteins.

The slides then are rinsed three (3) times in PBS. Next the slides are incubated in 100 µl secondary goat anti-rabbit antibody available, for example as Rabbit Detection System, Super Sensitive Concentrate, Biogenex, San Ramon, Calif., containing 2% normal human serum for twenty (20) minutes at room temperature. It should be noted that the goat anti-rabbit antibody is biotinylated goat anti-rabbit IgG concentrated link which is diluted prior to this use 1:100 in PBS containing 1% bovine serum albumin.

Next, the slides are rinsed three (3) times in PBS. The slides then are incubated in 100 µl of streptavidin-alkaline phosphatase available, for example as S-AP, Biogenex, San Ramon, Calif., for twenty (20) minutes at room temperature. The slides are then rinsed three (3) times in PBS.

b) Next, the slides are incubated with red chromogen stain, available for example as Stable Fast Red TR/Stable Naphthol Phosphate, Research Genetics, Inc., Huntsville, Ala. The chromogen is provided as two solutions which are mixed immediately before adding to the slides and 250 µl of the chromogen is added directly to the tissues and the slides are stained for seven and one-half (7½) minutes at 45° C. in a convection oven. It will be noted that the novel step of staining with the red chromogen stain makes possible the easy identification of Metallopanstimulin.

It should be noted that if staining is seen in the control slide containing no antibodies, i.e. false positive staining, Levamisole, available for example as Levamisole, Sigma Chemical, St. Louis, Mo., is added at a final concentration of 20 µg/ml to inhibit endogenous alkaline phosphatase that is present in certain tissues.

7. Final Rinses and Counter-staining

The slides are rinsed six (6) times in deionized water and then counterstained by dipping three times in hematoxylin, available, for example, from Richard-Allen Medical, Richland, Mich., and immediately rinsing six (6) times in water. Dip the slides in a standard "bluing solution", available, for example, as Bluing Reagent, Richard-Allen Medical. Although the preferred embodiment includes counterstaining with a blue reagent, it will be appreciated by those skilled in the art that an appropriate counterstain of a color other than red would be acceptable. The slides are mounted with aqueous mounting medium, available, for example as Geltol Aqueous Mounting Medium, Immunon/ Shandon, Pittsburgh, Pa., and viewed as appropriate.

The red chromagen staining and counterstaining allow a clinician to differentiate the presence of the MPS-1 protein from background staining, and allows for a quantification of the intensity of the staining, as set out above, with or without optical or computerized equipment. This aspect of the invention allows the novel technique to be used widely among clinicians in the field.

Figure 2:
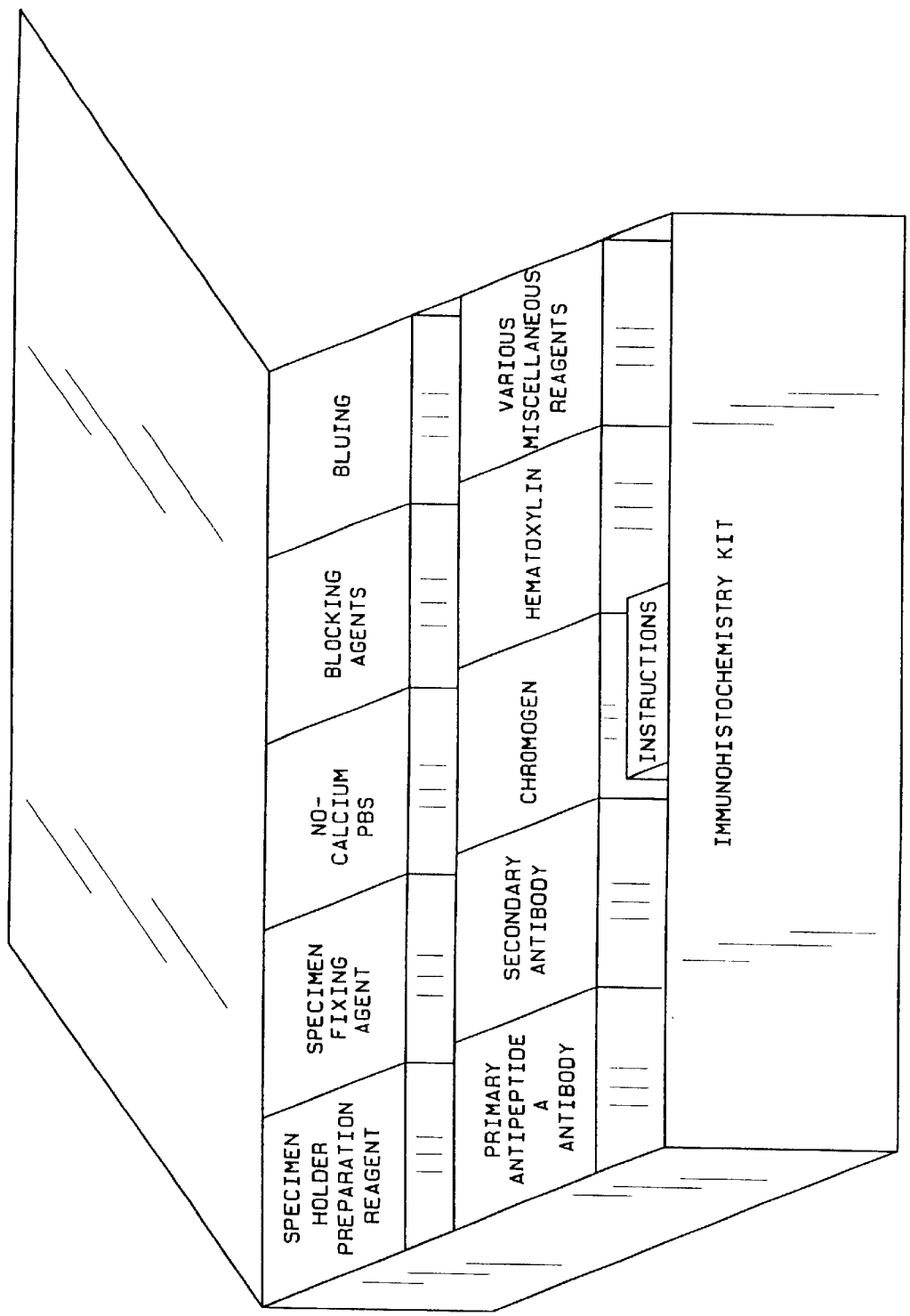
FIG. 2 is a perspective view of a basic kit for performing the method of the present invention.

It will be appreciated by those skilled in the art that the various materials used in the above described method can be provided in a kit form for use by laboratories or individual diagnosticians. The various reagents can be packaged in ready-to-use packaging in appropriate amounts for one tissue sample or multiple tissues samples as best shown in FIG. 2. The appropriate labeling, including step-by-step instructions can be include to allow the user to easily and conveniently practice the method of the present invention.

It also will be appreciated that although the method of the present invention was described in reference to immunohistochemistry staining of tissue to detect melanocytic and breast cancer lesions, the method can be used to detect the presence of other carcinomas and sarcomas, such as the those listed in Tables 1 and 2, above. Moreover, kits containing the described materials can be provided for testing of other tissues. Therefore, the foregoing description should be view as illustrative only and should not be construed in a limiting sense.

---

---

What is claimed is:

1. A method of detecting the presence of malignant melanoma cells in a tissue sample by detecting Metallopanstimulin (MPS-1) in the cytoplasm of said cells, said method comprising:

(a) fixing a tissue sample for staining with a buffered formalin having no detergent, thereby preserving the cytoplasmic MPS-1 protein;

(b) treating the tissue with a stain blocking agent;

(c) treating the tissue with a primary anti-peptide A antibody, said antibody having an affinity for an N-terminal portion of the MPS-1 protein, said N-terminal portion consisting of SEQ ID NO: 1, so that the antibody binds to the N-terminal portion, thereby forming an antibody MPS-1 complex;

(d) treating the tissue sample with a secondary anti-body having an affinity for said primary anti-peptide A antibody, so that the secondary antibody binds the primary antibody;

(e) treating the tissue sample with a red chromogen stain, thereby visibly distinguishing said antibody complexes from the surrounding tissues;

(f) counterstaining the tissue sample; and (g) visualizing the staining patterns to determine the presence of cytoplasmic MPS-1 wherein detection of cytoplasmic MPS-1 is indicative of the presence of malignant melanoma.

2. The method of claim 1 further comprising the step of indirectly determining the quantity of MPS-1 protein by detecting MPS-1/antibody complexes as a function of a red stain present in malignant cells compared to normal cells.

* * * * *

SEQUENCE LISTING (1) GENERAL INFORMATION:

(iii) NUMBER OF SEQUENCES: 1

(2) INFORMATION FOR SEQ ID NO: 1:

(i) SEQUENCE CHARACTERISTICS:
      (A) LENGTH: 16 amino acids
      (B) TYPE: amino acid
      (D) TOPOLOGY: linear (ii) MOLECULE TYPE: protein (xi) SEQUENCE DESCRIPTION: SEQ ID NO: 1:

Pro Leu Ala Lys Asp Leu Leu His Pro Ser Pro Glu Glu Glu Lys Arg
1         5                  10                 15